(12) United States Patent
Morgan et al.

(10) Patent No.: US 8,509,912 B2
(45) Date of Patent: Aug. 13, 2013

(54) EXTERNAL POWER SOURCE, SYSTEM AND METHOD FOR PREDICTING HEAT LOSS OF IMPLANTABLE MEDICAL DEVICE DURING INDUCTIVE RECHARGING BY EXTERNAL PRIMARY COIL

(75) Inventors: Boysie R. Morgan, Minneapolis, MN (US); David P. Olson, Minnetrista, MN (US); Andrew L. Schmeling, River Falls, WI (US)

(73) Assignee: Medtronic, Inc., Minneapolis, MN (US)

( * ) Notice: Subject to any disclaimer, the term of this patent is extended or adjusted under 35 U.S.C. 154(b) by 1474 days.

(21) Appl. No.: 12/112,394

(22) Filed: Apr. 30, 2008

(65) Prior Publication Data

US 2009/0276014 A1    Nov. 5, 2009

(51) Int. Cl.
*A61N 1/08* (2006.01)

(52) U.S. Cl.
USPC .................................. 607/61; 607/33; 607/60

(58) Field of Classification Search
USPC ............................................... 607/33, 60, 61
See application file for complete search history.

(56) References Cited

U.S. PATENT DOCUMENTS

| | | | |
|---|---|---|---|
| 5,411,537 A | 5/1995 | Munshi et al. | |
| 5,702,431 A | 12/1997 | Wang et al. | |
| 6,032,076 A | 2/2000 | Melvin et al. | |
| 6,067,474 A | 5/2000 | Schulman et al. | |
| 6,227,204 B1 | 5/2001 | Baumann et al. | |
| 6,327,504 B1 | 12/2001 | Dolgin et al. | |
| 6,430,444 B1 | 8/2002 | Borza | |
| 6,552,511 B1 | 4/2003 | Fayram | |
| 6,553,263 B1 | 4/2003 | Meadows et al. | |
| 6,894,456 B2 | 5/2005 | Tsukamoto et al. | |
| 7,009,362 B2 | 3/2006 | Tsukamoto et al. | |
| 2004/0098068 A1 | 5/2004 | Carbunaru et al. | |
| 2005/0021100 A1 | 1/2005 | Tsukamoto et al. | |
| 2005/0075693 A1 | 4/2005 | Toy et al. | |
| 2005/0075700 A1* | 4/2005 | Schommer et al. | 607/61 |
| 2005/0119716 A1* | 6/2005 | McClure et al. | 607/61 |
| 2006/0085041 A1* | 4/2006 | Hastings et al. | 607/33 |
| 2006/0247737 A1* | 11/2006 | Olson et al. | 607/61 |

FOREIGN PATENT DOCUMENTS

WO    WO 2008/012523 A2    1/2008

OTHER PUBLICATIONS

International Search Report for PCT/US2009/030988.

* cited by examiner

*Primary Examiner* — Carl H Layno
*Assistant Examiner* — Jennifer Ghand
(74) *Attorney, Agent, or Firm* — IPLM Group, P.A.

(57) ABSTRACT

External power source, system for controlling and method for predicting heat loss of implantable medical device during inductive recharging by an external primary coil. A primary coil inductively couples energy to a secondary coil when energized and placed in proximity of the secondary coil. Control circuitry, operatively coupled to said primary coil, determines the energy absorbed in said tissue based on a total applied power by said external power source, power lost in said electronic circuitry, power lost in said electronic circuitry, power lost in said primary coil and power applied to said rechargeable power source and controlling said total applied power based upon said energy absorbed in said tissue.

21 Claims, 7 Drawing Sheets

EXTERNAL POWER SOURCE, SYSTEM AND METHOD FOR PREDICTING HEAT LOSS OF IMPLANTABLE MEDICAL DEVICE DURING INDUCTIVE RECHARGING BY EXTERNAL PRIMARY COIL

FIELD

The present invention relates generally to controllers, systems and methods for implantable medical devices and, more particularly, to such controllers, systems and methods for implantable medical devices having a rechargeable power supply.

BACKGROUND

The medical device industry produces a wide variety of implantable electronic devices for treating patient medical conditions. For some medical conditions, medical devices provide the best, and sometimes the only, therapy to restore an individual to a more healthful condition and a fuller life. Examples of implantable medical devices designed to deliver therapeutic electrical stimulation include neurological stimulators, pacemakers and defibrillators.

One of the common benefits of implantable medical devices is that once the device has been surgically implanted, and the surgical incisions created in the patient's skin closed up, the device may function without requiring a physical interface with devices external to the patient. This creates compelling benefits to the patient by preventing the discomfort and risk of infection inherent in various articles projecting through cuts in the patient's skin. However, the inaccessibility inherent in a device that has been surgically implanted creates several challenges. Not the least of these challenges is providing power for active electrical componentry in the device.

The problem of providing electrical power to components contained in a hermetically sealed case implanted in a patient's body has been addressed to varying degrees of success in the preceding decades through advances in battery technology. In some implantable medical device applications the increased longevity and efficiency of modern batteries has been supplemented with the ability to recharge the battery via an inductive link. But the challenges and risks inherent in any effort to inductively transfer energy from a coil connected to an external charger to a coil connected to the battery of an implantable medical device through the skin and tissue of a patient have made applications of inductive recharging of implantable medical devices relatively uncommon in the industry.

The passing of energy through the skin and tissue of a patient to the implantable medical device may tend to result in some of the energy being dissipated in the form of heat in the patient's skin and tissue. Improving the inductive connection between the external charger and the implantable medical device by positioning the external coil in the closest possible proximity to the implantable medical device will help to minimize energy dissipation, but cannot eliminate it. Further, additional energy may be dissipated as heat through the case of the implantable medical device itself. This issue may tend to be exacerbated by the trend of steadily decreasing the size of medical devices, as a smaller case results in the increased density of the energy escaping, and thus greater heat. It is possible that a patient experiencing unchecked inductive energy transfer to their implantable medical device may experience significant discomfort and even potentially severe skin and tissue burns.

Thus, limitations are typically placed on the amount of energy that may be transferred per unit time to an implantable medical device. These limits are arrived at partially as a function of the size of the device and partially by incorporating an amount of presumed variance in the positioning of the external charger relative to the implantable medical device. Thus, even if the external charger is placed in a position that would result in comparatively little energy dissipation in the skin and tissue, the amount of energy that would be delivered by the external charger would still be limited by the assumed worst-case safety factors.

Efforts to empirically measure the amount of heat that is being generated in a patient's tissue during energy transfer have sometimes proven to be inaccurate and/or impractical. The mounting of a temperature sensor on the outside of the case of an implantable medical device has only limited utility because it measures only the temperature at that particular point and might not be sensitive to local hotspots and could be inconvenient by necessitating running a wire through the case.

SUMMARY

Embodiments address the issue of determining the amount of energy dissipated in a patient, not by measuring energy dissipation from the perspective of the implantable medical device, but by measuring characteristics of the energy transfer from the perspective of the external charger. This is based on the recognition that applied power from the external power supply must go to one of four places: it must be lost in the external coil, it must be lost in the voltage regulator of the external charger or associated circuitry such as driving circuitry for the regulator, it must be lost in the tissue of the patient, or it must end up as useable energy in the battery of the implantable medical device. The loss in the voltage regulator is a known value of any voltage regulator. The energy in the battery is a value that is frequently measured and known by the implantable medical device. Thus, by determining the energy lost in the primary coil, the amount of energy dissipated as heat may be calculated.

Power equals a square of the current multiplied by the resistance. However, measuring the current in the primary coil directly is difficult. Thus, the current may be determined indirectly. An H-bridge circuit drives the primary coil at a known voltage. By solving for the current based on a known applied power and a selected pulse width and frequency, the current through the H-bridge circuit may be determined, and it is known that this is the current through the coil. The energy lost in the primary coil may then be determined, followed by the energy dissipated as heat.

This result is determined by a control circuitry in the external charger. If the result indicates more heat energy than an allowable maximum, the control circuitry may reduce the applied power, thereby reducing the heat energy. If the result indicates that the patient could safely withstand greater heat dissipation, the applied power may be increased to a point where the dissipated heat remains safe. In this manner, a patient may always conduct battery recharging procedures at the maximum safety and efficiency.

In an embodiment, an external power source for an implantable medical device has a secondary coil operatively coupled to a rechargeable power source. A primary coil inductively couples energy to the secondary coil when energized and placed in proximity of the secondary coil. Control circuitry, operatively coupled to a primary coil, determines the energy absorbed in the tissue based on a total applied power by the external power source, power lost in the electronic circuitry, power lost in the electronic circuitry, power lost in the primary coil and power applied to the rechargeable power source and controls the total applied power based upon the energy absorbed in the tissue.

In an embodiment, an external power source inductively charges an implantable medical device in a patient. Control circuitry, operatively coupled to electronic circuitry driving a primary coil, controls energy absorbed in the patient during inductive charging of the rechargeable power source by (a) determining a total applied power by the external power source by measuring current applied by the external power source during the charging and an applied voltage of the external power source, (b) determining power lost in the electronic circuitry, (c) determining power lost in the primary coil by measuring current in the primary coil during the recharging in view of a resistance of the primary coil, (d) determining power applied to the rechargeable power source by measuring the voltage of the rechargeable power source and current applied to the rechargeable power source during the inductive charging, (e) calculating the energy absorbed in the body by subtracting the power lost in the electronic circuitry, the power lost in the primary coil and the power applied to the rechargeable power source from the total applied power and (f) adjusting the total applied power by the external power source as a function of the energy absorbed in the patient.

In an embodiment, a system controls energy absorbed in a patient during inductive charging. An implantable medical device has therapeutic componentry delivering a therapeutic output to the patient, a rechargeable power source operatively coupled to the therapeutic componentry and a secondary coil operatively coupled to the rechargeable power source. An external power source has a primary coil and control circuitry, operatively coupled to electronic circuitry driving the primary coil, controlling energy absorbed in the patient during inductive charging of the rechargeable power source by (a) determining a total applied power by the external power source by measuring current applied by the external power source during the charging and an applied voltage of the external power source, (b) determining power lost in the electronic circuitry, (c) determining power lost in the primary coil by measuring current in the primary coil during the recharging in view of a resistance of the primary coil, (d) determining power applied to the rechargeable power source by measuring the voltage of the rechargeable power and current applied to the rechargeable power source during the inductive charging, (e) calculating the energy absorbed in the body by subtracting the power lost in the electronic circuitry, the power lost in the primary coil and the power applied to the rechargeable power source from the total applied power and (f) adjusting the total applied power by the external power source as a function of the energy absorbed in the patient.

In an embodiment, a method of determines energy absorbed in a body during inductive charging of an implantable medical device having a rechargeable power source having a voltage and a secondary coil operatively coupled to the rechargeable power source by an external power source having electronic circuitry driving a primary coil. A total applied power by the external power source is determined by measuring current applied by the external power source during the charging and an applied voltage of the external power source. Power lost in the electronic circuitry is determined. Power lost in the primary coil is determined by measuring current in the primary coil during the recharging in view of a resistance of the primary coil. Power applied to the rechargeable power source is determined by measuring the voltage of the rechargeable power and current applied to the rechargeable power source during the inductive charging. The energy absorbed in the body is calculated by subtracting the power lost in the electronic circuitry, the power lost in the primary coil and the power applied to the rechargeable power source from the total applied power.

In an embodiment, a method adjusts an amount of energy dissipated in a patient during inductive charging of an implantable medical device having a rechargeable power source having a voltage and a secondary coil operatively coupled to the rechargeable power source. The energy is provided by an external power source having electronic circuitry driving a primary coil. A total power applied by the external power source is determined by measuring current applied by the external power source during the charging and an applied voltage of the external power source. Power lost in the electronic circuitry is determined. Power lost in the primary coil is determined by measuring current in the primary coil during the recharging in view of a resistance of the primary coil. Power applied to the rechargeable power source is determined by measuring the voltage of the rechargeable power source and current applied to the rechargeable power source during the inductive charging. The energy absorbed in the patient is calculated by subtracting the power lost in the electronic circuitry, the power lost in the primary coil and the power applied to the rechargeable power source from the total applied power. The total power applied by the external power source is adjusted as a function of the energy absorbed in the patient.

In an embodiment, the power lost in the primary coil is calculated by multiplying the current in the primary coil during the charging by a square of the resistance of the primary coil, the external power source supplies power, having a current and a voltage, to the electronic circuitry, wherein the total applied power is calculated by multiplying the current supplied by the external power source during the charging by the voltage supplied by the external power source. The power applied to the rechargeable power source is calculated by multiplying the current applied to the rechargeable power source during the charging by the voltage of the rechargeable power source.

In an embodiment, the voltage supplied by the external power source comprises an RMS voltage, wherein the RMS voltage supplied by the external power source and the current supplied by the external power source have a phase difference and wherein the determining the total applied power comprises calculating the total applied power by multiplying the current supplied by the external power source during the charging by the RMS voltage supplied by the external power source and further multiplying by a power factor representative of the phase difference.

In an embodiment, power lost in the electronic circuitry is determined empirically.

In an embodiment, the power lost in the electronic circuitry is approximately fifteen percent (15%) of the total applied power.

DRAWINGS

DESCRIPTION

Figure 1:
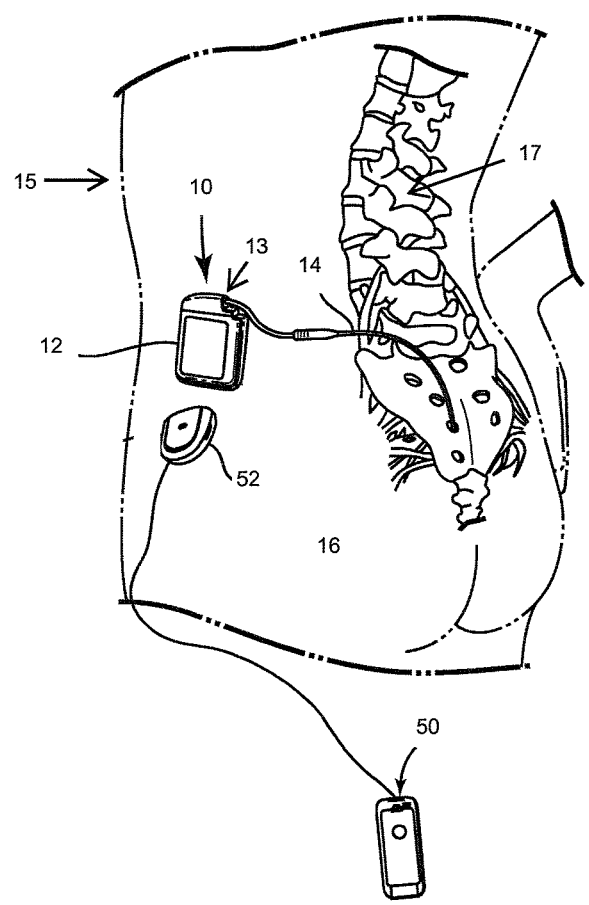
FIG. 1 shows an example of an implantable neurological stimulator implanted in the side of a patient, with electrodes positioned along the patient's spinal cord.

FIG. 1 shows the general environment of one rechargeable implantable medical device 10 embodiment. Implantable neurological stimulator 12 is shown, but other embodiments such as pacemakers and defibrillators and the like are also applicable. Implantable neurological stimulator 12 is implanted subcutaneously in side 16 of patient 15. Lead 14 is operatively coupled to implantable neurological stimulator 12 at header 13, and is positioned along spinal chord 17 of patient 15. Charging unit 50, which may be a physician programmer or patient programmer, may become transcutaneously coupled to implantable neurological stimulator 12 via an inductive communication link through the tissue of patient 15 when external antenna 52 is placed in proximity to implantable neurological stimulator 12.

Figure 2:
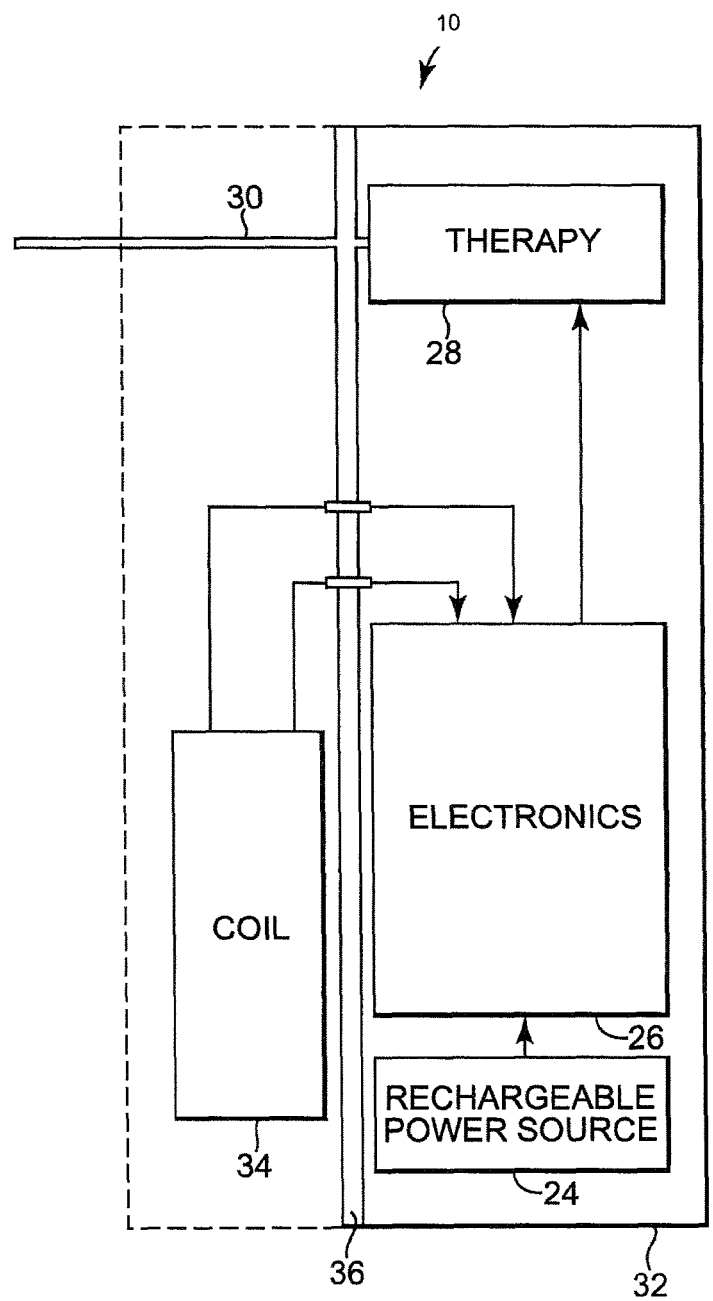
FIG. 2 shows an external charger and inductive telemetry coil for delivering charge to an implantable medical device.

In FIG. 2, implantable medical device 10, of which implantable neurological simulator is a specific possible embodiment, has a rechargeable power source 24, such as a Lithium ion battery, powering electronics 26 and therapy module 28 in a conventional manner. Therapy module 28 is coupled to patient 15 through one or more therapy connections 30, also conventionally. Rechargeable power source 24, electronics 26 and therapy module 28 are contained in hermetically sealed housing 32. Secondary charging coil 34 is attached to the exterior of housing 32. Secondary charging coil 34 is operatively coupled through electronics 26 to rechargeable power source 24. In an alternative embodiment, secondary charging coil 34 could be contained in housing 32 or could be contained in a separate housing umbilically connected to electronics 26. Electronics 26 help provide control of the charging rate of rechargeable power source 24 in a conventional manner. Magnetic shield 36 (optional) is positioned between secondary charging coil 34 and housing 32 in order to protect rechargeable power source 24, electronics 26 and therapy module 28 from electromagnetic energy when secondary charging coil 34 is utilized to charge rechargeable power source 24.

Rechargeable power source 24 can be any of a variety power sources including a chemically based battery or a capacitor. In a preferred embodiment, rechargeable power source is a well known lithium ion battery.

Figure 3:
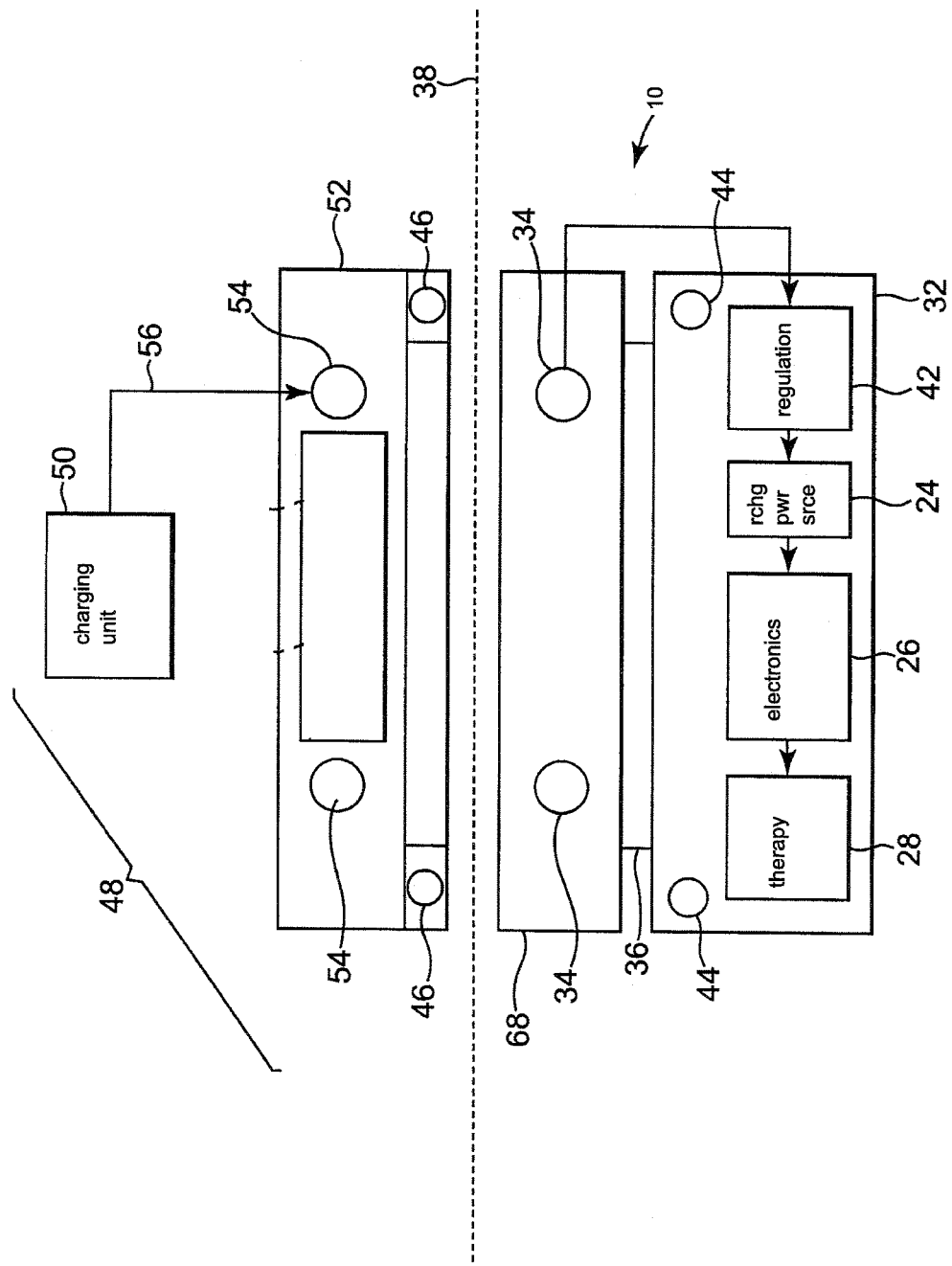
FIG. 3 shows a block diagram of an external charger and an implantable neurological stimulator.

FIG. 3 illustrates an alternative embodiment of implantable medical device 10 situated under cutaneous boundary 38. Implantable medical device 10 is similar to the embodiment illustrated in FIG. 2. However, charging regulation module 42 is shown separate from electronics 26 controlling therapy module 28. Again, charging regulation and therapy control is conventional. Implantable medical device 10 also has internal telemetry coil 44 configured in conventional manner to communicate through external telemetry coil 46 to an external programming device (not shown), charging unit 50 or other device in a conventional manner in order to both program and control implantable medical device 10 and to externally obtain information from implantable medical device 10 once implantable medical device 10 has been implanted. Internal telemetry coil 44 may be rectangular in shape with dimensions of 1.85 inches (4.7 centimeters) by 1.89 inches (4.8 centimeters) constructed from 150 turns of 43 AWG wire, and may be sized to be larger than the diameter of secondary charging coil 34 (in internal antenna 68). Secondary coil 34 may be constructed with 182 turns of 30 AWG wire with an inside diameter of 0.72 inches (1.83 centimeters) and an outside diameter of 1.43 inches (3.63 centimeters) with a height of 0.075 inches (0.19 centimeters). Magnetic shield 36 is positioned between secondary charging coil 34 and housing 32 and is sized to cover the footprint of secondary charging coil 34.

Internal telemetry coil 44, having a larger diameter than secondary coil 34, is not completely covered by magnetic shield 36 allowing implantable medical device 10 to communicate with the external programming device with internal telemetry coil 44 in spite of the presence of magnetic shield 36.

Rechargeable power source 24 can be charged while implantable medical device 10 is in place in a patient through the use of external charging device 48. In an embodiment, external charging device 48 consists of charging unit 50 and external antenna 52. Charging unit 50 contains the electronics necessary to drive primary coil 54 with an oscillating current in order to induce current in secondary coil 34 when primary coil 54 is placed in the proximity of secondary coil 34. Charging unit 50 is operatively coupled to primary coil by cable 56. In an alternative embodiment, charging unit 50 and antenna 52 may be combined into a single unit. Antenna 52 may also optionally contain external telemetry coil 46 which may be operatively coupled to charging unit 50 if it is desired to communicate to or from implantable medical device 10 with external charging device 48. Alternatively, antenna 52 may optionally contain external telemetry coil 46 which can be operatively coupled to an external programming device, either individually or together with external charging unit 48.

Figure 4:
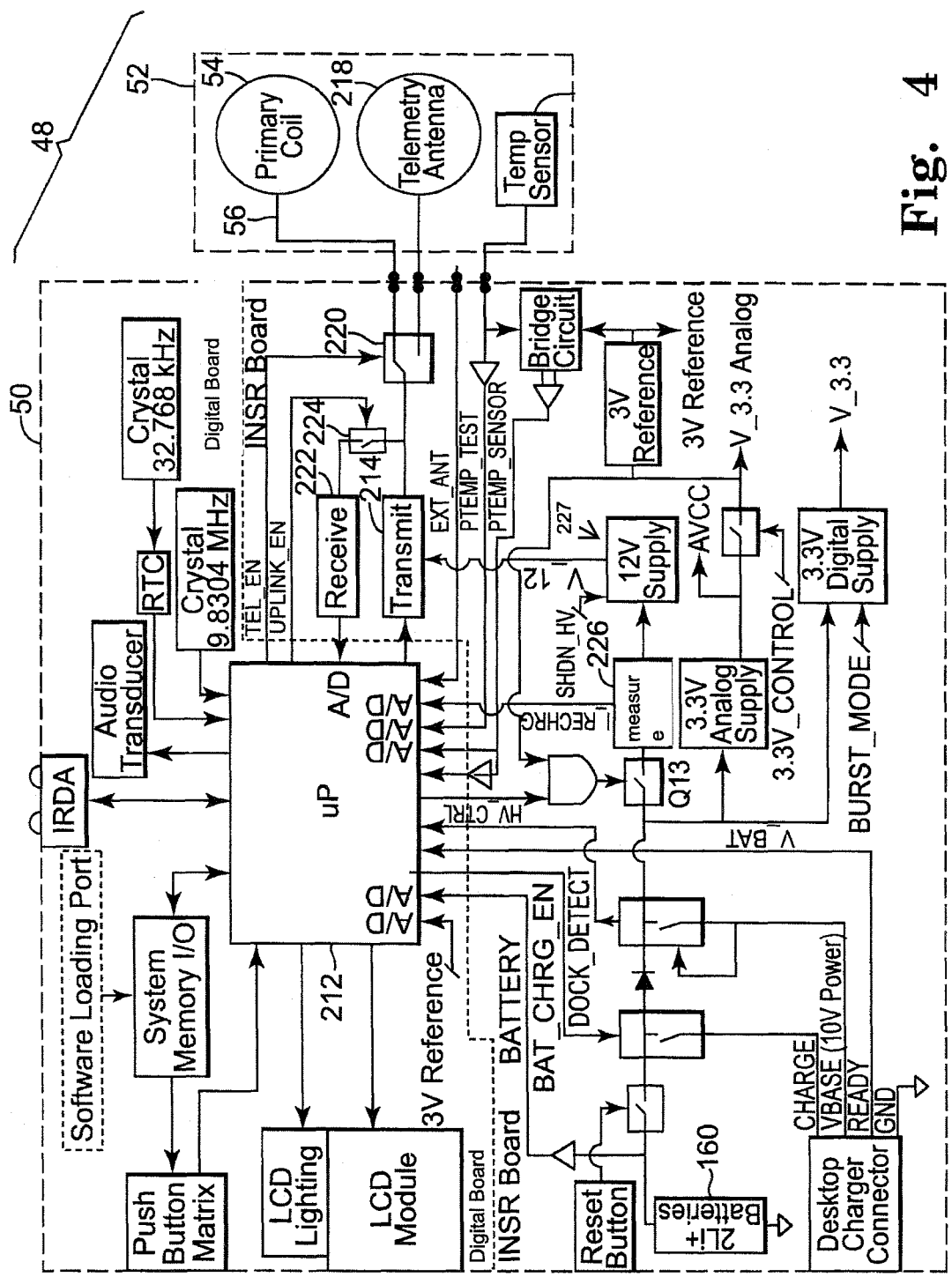
FIG. 4 shows a block diagram of an external charger.

FIG. 4 shows a block diagram of external charging device 48 controlled by microprocessor 212. Transmit block 214 consists of an H-bridge circuit powered from 12 volt power supply 227. Transmit block 214 drives primary coil 54 in external antenna 52. H-bridge control signals and timing are provided conventionally by microprocessor 212. H-bridge circuit in transmit block 214 is used to drive both primary coil 54 for power transfer and/or charging, and telemetry antenna 218. Drive selection is done by electronically controllable switch 220. In one embodiment, during power transfer and/or charging, H-bridge circuit is driven at 9 kiloHertz. During telemetry, H-bridge circuit is driven at 175 kiloHertz.

Receive block 222 is used during telemetry, enabled by switch 224, to receive uplink signals from implanted medical device 10. Twelve volt power supply 227 is a switching regulator supplying power to transmit block 214 during power transfer and/or charging as well as telemetry downlink. Nominal input voltage to 12 volt power supply 227 is either 7.5 volts from lithium ion batteries 160 or 10 volts from an outside voltage source.

Current measure block 226 measures current to 12 volt power supply 227. Current measured by current measure block 226 is used in the calculation of battery 160 voltage, as well as current into battery 160. As noted above, "power in" is used in the calculation of efficiency of power transfer and/or charging efficiency to determine, in part, the best location of external antenna 52.

In an embodiment, during a power transfer, primary coil 54 is energized using transmit circuit 214, which drives an output current from 12V supply 227 at approximately nine kiloHertz, as noted above. The current through 12V supply 227 is measured using current measure 226. The amount of current delivered to transmit circuit 214, and there on to primary coil 54, may primarily determine the amount of time required to charge rechargeable power source 24. While outside factors such as the efficiency of the coupling between primary coil 54 and secondary coil 34 may place an upper bound on the amount of energy that may be transferred per unit time during charging, as a practical matter the amount of energy actually transferred to implantable medical device 10 per unit time may be principally governed by the amount of current through transmit circuit 214 and primary coil 54. Higher current thus may generally lead to lower charge times, which is desirable for patient 15, who may therefore spend less time recharging rechargeable power source 24.

However, the greater the current through transmit circuit 214, the greater energy that is transferred, and the more energy that may tend to be dissipated in the various components before the energy reaches rechargeable power source 24. Energy that is dissipated rather than stored may tend to be dissipated as heat, and the more energy that is dissipated in a given time, the greater the heat buildup may tend to be. Components of charging unit 50 may have little relevant impact. Energy dissipated as heat in charging unit 50 and between antenna 52 and rechargeable power source 24 may ultimately tend to transfer to tissue of patient 15. Heat buildup may tend to cause patient discomfort and even injury if tissue of patient 15 is damaged. As such, limits on the total amount of current that may be driven through primary coil 54 are commonly based on highly conservative estimates of the amount of energy that may be dissipated for any given driven current. Thus, charging may be limited overall in order to prevent heat build up from dissipated energy. In an exemplary embodiment, energy dissipation is generally limited to 342 milliWatts. It has been determined empirically that the amount of current delivered to transmit circuit 214 that corresponds to a heat dissipation of 342 milliWatts is 50 milliAmps under the most disadvantageous possible circumstances. Thus, charging current is limited to not exceed 50 milliAmps.

However, as noted, the estimates are commonly highly conservative and do not take into account potential mitigating factors, such as the fact that energy dissipation may occur in components, particularly those of charging unit 50, that may not negatively impact patient 15. Thus, in an embodiment, heat buildup is determined based not on conservative estimates of energy dissipation throughout the system, but based on characterizing the system and determining how much of the dissipated energy is dissipated in locations that could be detrimental to patient safety.

Energy dissipated as heat may ultimately end up either dissipated to charging unit 50 or the atmosphere or such heat may be dissipated as heat in the tissue of patient 15. Energy may be dissipated in the internal components of charging unit 50 and antenna 52. Energy dissipated within charging unit 50 may primarily result from dissipation within transmit circuit 214, which comprises an H-bridge circuit. The physical characteristics of transmit circuit 214 may result in a known percentage of input energy being dissipated, some of which may be dissipated as heat energy. Energy dissipated as heat in antenna 52, particularly that dissipated within primary coil 54, may with appropriate ventilation known in the art be dissipated into the atmosphere.

It is desirable not to dissipate energy as heat either directly in tissue of patient 15 or within implantable medical device 10. It is desirable that such heat dissipation be determined and regulated. Energy dissipated within implantable medical device 10 may ultimately heat tissue of patient 15 by transmitting through housing 32, which may be comprised of a thermally conductive metal, such as titanium.

Thus, it can be seen that the energy that first passes through current measure 226 in charging unit 50 ultimately ends up delivered to rechargeable power source 24, ends up being dissipated in the components of charging unit 50, or dissipated as heat in tissue of patient 15, either directly or via heating of components of implantable medical device 10. It is possible to determine the energy delivered to rechargeable power source 24 by measuring the charging current through charging regulation module 42 and measuring the battery voltage using componentry commonly known in the art. It is also possible to calculate the energy dissipation caused by the internal componentry of charging unit 50, transmit circuit 214 in particular, by characterizing the dissipation characteristics of charging unit 50. However, the energy dissipated as heat to patient 15 is not possible to know directly, because energy may be dissipated directly in the tissue, or energy may be dissipated within implantable medical device 10 differently dependent on difficult to determine factors such as the moment-by-moment positioning of primary coil 54 relative to implantable medical device 10, among other variables. Further, it may not be possible to know how much energy is actually being dissipated in primary coil 54 without measuring the current through primary coil 54. However, when current is attempted to be measured accurately, there may be an unavoidable impact to the delivery of energy to the intended destination, due to the need to divert energy in order to measure the current in the first place.

The power source for charging unit 50 may be the source of energy for the system comprised of charging unit 50 and implantable medical device 10. Some of the energy that is inputted in the system may be dissipated in charging unit 50 or stored in rechargeable power source. The rest of the energy that is inputted into the system may either be dissipated in primary coil 54 or in patient tissue. However, as noted above, it may not be possible to measure the energy dissipated in primary coil 54. Likewise, if any physical means exist for measuring energy dissipation in human tissue, the measurement means may be invasive or harmful to patient 16.

If it cannot be determined how much energy is being dissipated in primary coil 54 and not tissue, then concern for patient safety may require an assumption that all of the energy that is input into the system that is not either dissipated in charging unit 50 or stored in rechargeable power source 24 is in fact dissipated in tissue. A necessary corollary to such an assumption is that primary coil 54 dissipates no energy at all, which is plainly unlikely to occur in reality. However, such an assumption may be necessary in order to decrease the likelihood of injury to patient 16. Thus, unless a reasonable approximation of energy dissipation in primary coil 54 may be determined, the total energy of the system may have to be reduced in order to reduce the risk of injury to patient 16.

Figure 5A:
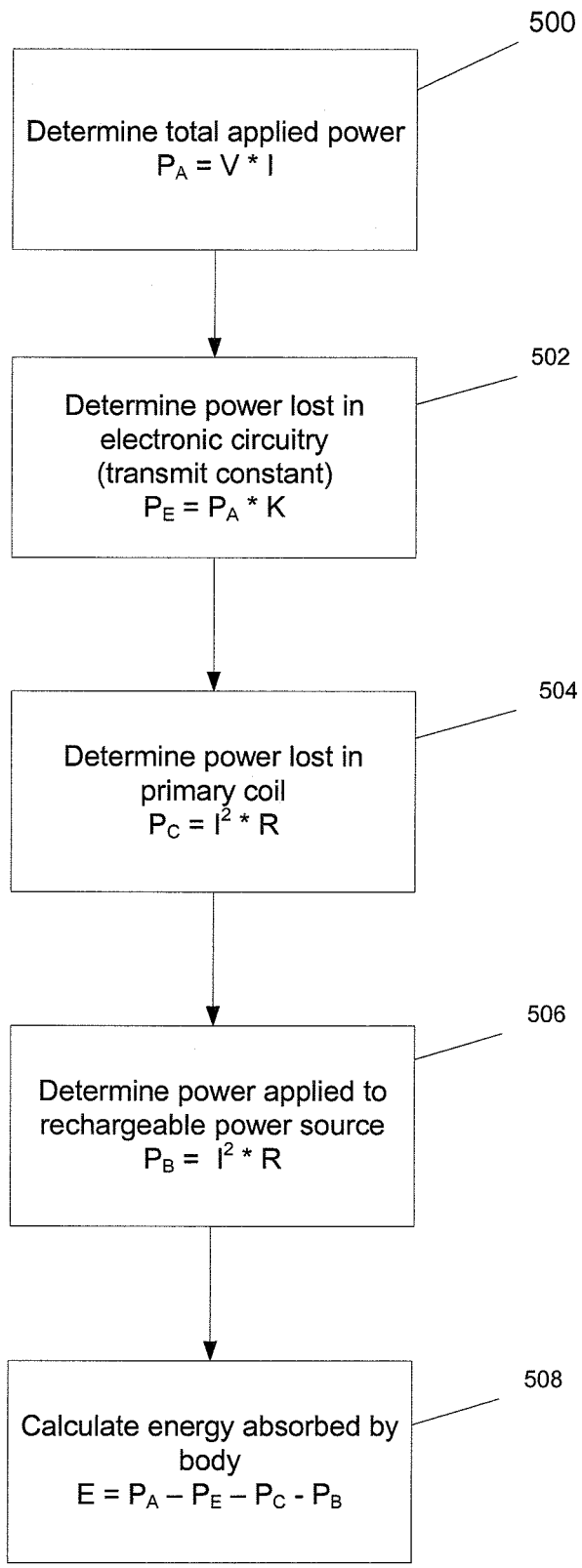
FIGS. 5a and 5b are flowcharts illustrating the determination of energy absorbed by the body.

FIG. 5a is a flowchart for determining energy dissipated as heat in patient tissue or, said in another way, the amount of heat absorbed in the body. The total applied power is the power supplied to drive primary coil 54. The total applied power is determined (500) by multiplying the measured voltage (V) at transmit block 214 by the current driven into transmit block 214. The result is the total power available to drive primary coil 54 but some power is in the electronic driving circuitry and in the voltage regulator. The amount of power dissipated by the driving electronics and in voltage regulation is difficult to determine and, hence, can be developed empirically. The empirically derived power loss can be expressed as percentage loss or, alternatively, as a percentage of the total applied power or a fraction. It has been determined by experiment that the amount of power lost in voltage regulation to be about fifteen percent (15%) and a few additional percent may be lost in the driving circuitry. This power loss can be expressed as a constant of from 0.80 to 0.85. That is, from eighty percent (80%) to eighty-five percent (85%) of the total applied power actually is passed through to primary coil 54. Thus, the power lost in the electronic circuitry (voltage regulation and driving circuitry) can be determined (502) by multiplying the total applied power times the transmit constant, e.g., 0.80 to 0.85 as examples. The transmit circuit constant may vary from embodiment to embodiment, dependent on the characteristics of transmit block 214.

In an embodiment, the voltage supplied by the external power is an RMS voltage having a phase difference with current supplied by the external power source. In this situation, the total applied power may be calculated by multiplying the current supplied by the external power source during charging by the RMS voltage supplied by the external power source and further multiplying the result by a power factor representative of the phase difference.

Figure 5B:
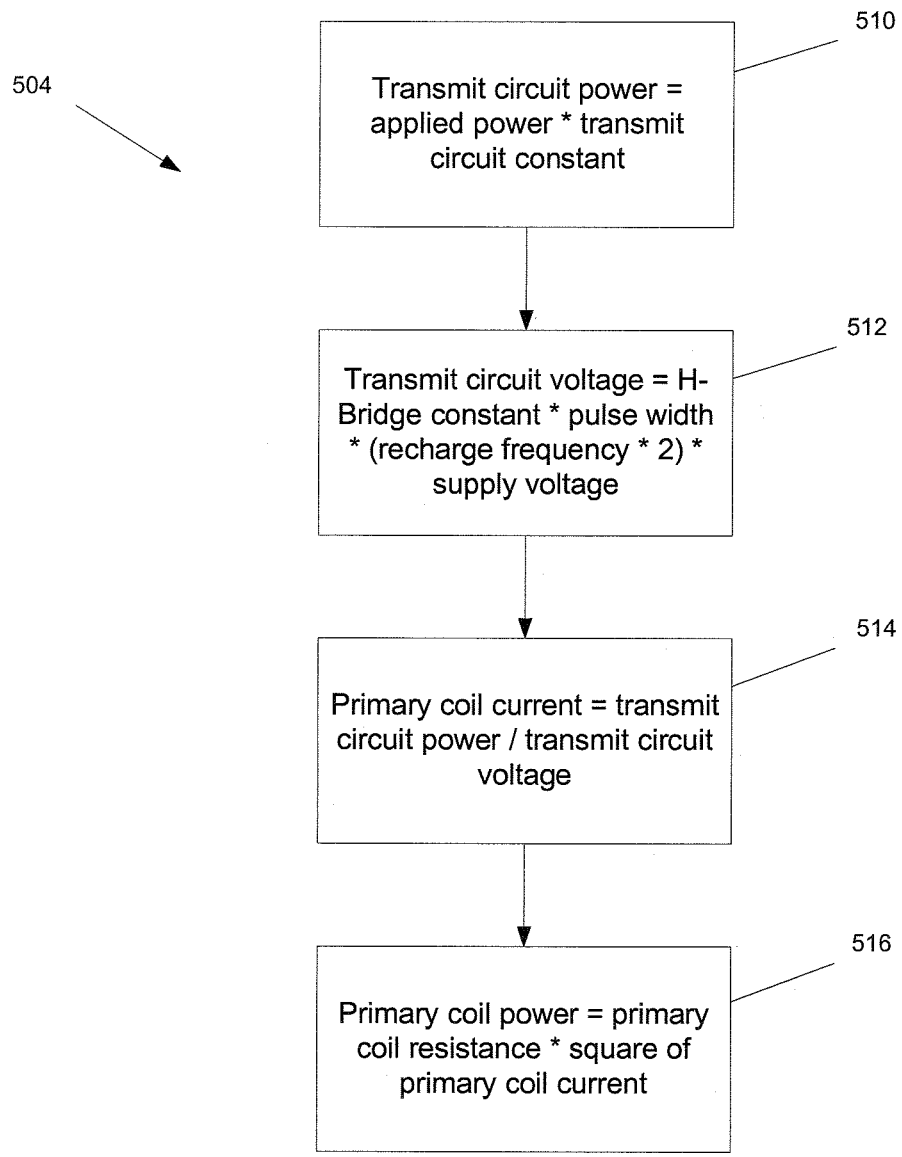

Power lost or dissipated in primary coil 54 is then determined (504) in FIG. 5a, which is set out in more detail in FIG. 5b.

Transmit circuit power equals applied power times transmit circuit constant (510). The transmit circuit voltage equals the voltage delivered to primary coil 54 and may be determined (512) by multiplying the duty cycle of the voltage in primary coil 54 by the input voltage and scaling the voltage with an H-Bridge constant related to the characteristics of the H-Bridge of transmit block 214. In an embodiment, the H-Bridge constant is 1.27. The duty cycle may be determined by the relationship Duty Cycle=pulse width*$f$*2.

The current in primary coil 54 may be determined (514) by dividing the transmit circuit power (500) by the transmit circuit voltage (512). Primary coil power dissipation may then be determined (516) utilizing the relationship $P=I^2*R$ by multiplying a square of primary coil current (514) by a measured value of the primary coil resistance.

Returning to FIG. 5a, the power applied or delivered to rechargeable power source 24 may be determined (506) by measuring the charge current to rechargeable power source. The known or measured resistance of the rechargeable power source can then be multiplied by a square of charge current to determine the power applied to the rechargeable power source.

Having determined total applied power (500), power lost in electronic circuitry (502), power dissipated or lost in the primary coil (504) and the power actually delivered to the rechargeable power source (506), the remaining power from the total applied power after accounting for (subtracting) the power lost in electronic circuitry, the power lost in the primary coil and the power delivered to the rechargeable power is the power or energy absorbed in the body. Thus, power absorbed in the body is determined (508) by subtracting the power lost delivered to the rechargeable power source and the power lost in the primary coil and the power lost in the electronics from the total applied power.

Figure 6:
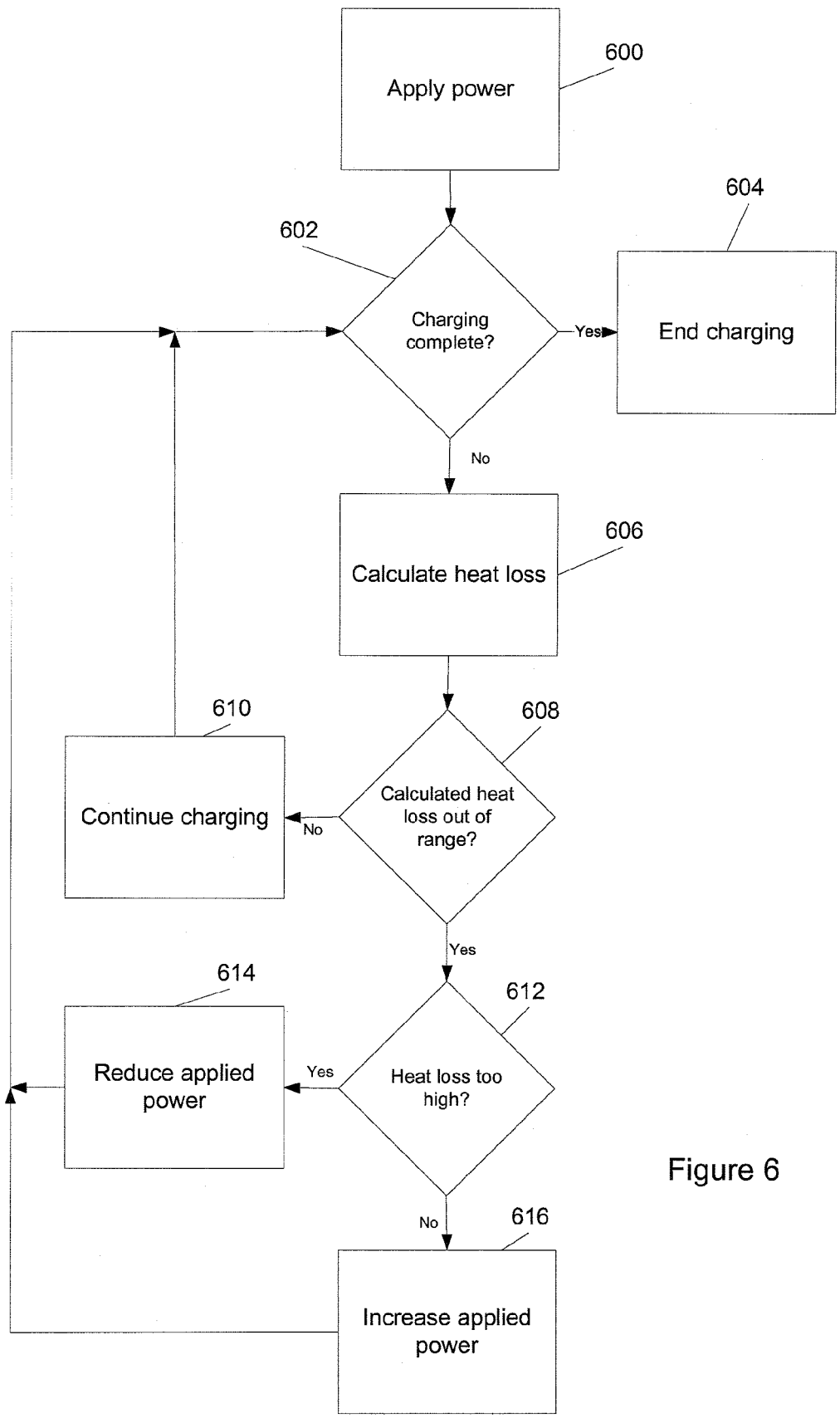
FIG. 6 shows a flowchart for adjusting applied power in order to regulate the amount of energy absorbed by the body.

FIG. 6 is a flowchart for adjusting applied power in order to regulate the amount of energy dissipated as heat in tissue of patient 15. A recharging session is initiated (600) by applying power to rechargeable implantable medical device 10. Periodically during charging, the amount of charge in battery 24 is measured (602), and if battery 24 has sufficient charge the charging session ends (604). If battery 24 is not yet fully charged, heat loss is then calculated (606) according to the method of FIG. 5a. The calculated heat loss is then compared (608) against a predetermined maximum. The predetermined maximum may depend on a variety of factors unique to various implantable medical devices, such as the surface area of housing 32 and the physical characteristics of the components of implantable medical device 10. In an embodiment, this predetermined maximum is 250 milliWatts.

In an embodiment, if the calculated heat loss is within (608) the predetermined range then charging continues as normal (610) until the next periodic check of battery 24 charge (602). If the calculated heat loss is higher (612) than the predetermined range, applied power is reduced (614) by an amount proportional to the degree to which the calculated heat loss is too high. If the calculated heat loss is lower than the predetermined range, applied power is increased (616) by an amount proportional to the degree to which the calculated heat loss is too low. Thus, by way of example, if heat dissipation power should be a minimum of 198 milliWatts, but is determined to be 178 milliWatts, and total applied power was 625 milliWatts, and thus 28.5% of applied power was being dissipated as heat, then applied power may be increased by 20 milliWatts/0.285, or approximately 70 milliWatts. In either case, charging then proceeds until the next periodic check of battery 24 charge (602).

In another embodiment, in order to avoid exceeding the predetermined maximum heat loss, charging is started at a predetermined, relatively low power level and the energy absorbed by the body is determined as discussed above. If the energy absorbed by the body is below the predetermined maximum, then the power level is increased in a predetermined step amount, e.g., 20 milliWatts, or a predetermined percentage, e.g., ten percent (10%) and the energy absorbed by the body is again calculated. This iterative process may be continued until the calculated energy absorbed by the body approaches or reaches the predetermined maximum. If the calculated energy absorbed in the body reaches or exceeds the predetermined maximum, the power level may be decreased or charging may be terminated until the energy absorbed by the body returns to acceptable levels.

In these ways, an charging may be accomplished at the maximum power level, and, hence, shortest time, possible while still maintaining patient safety by knowing and limiting the energy absorbed by the body.

Of course, it is recognized that the above described embodiment is merely an embodiment for calculating energy dissipation as heat in patient tissue and of adjusting applied power based on the determined heat dissipation. For instance, an embodiment where the energy dissipation within primary coil may be determined by measuring current through primary coil directly is also envisioned. Alternatively, embodiments where current through primary coil is determined using characteristics other than those of the H-bridge of transmit circuit are likewise envisioned.

Thus, embodiments of the external power source, system and method for predicting heat loss of implantable medical device during inductive recharging by external primary coil are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. An external power source for an implantable medical device having a secondary coil operatively coupled to a rechargeable power source, said implantable medical device being implanted in a patient having tissue, comprising:
   a primary coil inductively coupling energy to said secondary coil when energized and placed in proximity of said secondary coil;
   electronic circuitry driving said primary coil; and
   control circuitry, operatively coupled to said primary coil, configured to determine energy absorbed in said tissue based on a total applied power by said external power source, power lost in said electronic circuitry, power lost in said primary coil and power applied to said rechargeable power source and control said total applied power based upon said energy absorbed in said tissue.

2. An external power source for inductively charging of an implantable medical device in a patient, said implantable medical device having a rechargeable power source having a voltage and a secondary coil operatively coupled to said rechargeable power source, comprising:
- a primary coil;
- electronic circuitry driving said primary coil; and
- control circuitry, operatively coupled to said electronic circuitry, configured to control energy absorbed in said patient during inductive charging of said rechargeable power source by:
  - determining a total applied power by said external power source by measuring current applied by said external power source during said charging and an applied voltage of said external power source;
  - determining power lost in said electronic circuitry;
  - determining power lost in said primary coil by determining current in said primary coil during said recharging in view of a resistance of said primary coil;
  - determining power applied to said rechargeable power source by measuring said voltage of said rechargeable power and current applied to said rechargeable power source during said inductive charging;
  - calculating said energy absorbed in said body by subtracting said power lost in said electronic circuitry, said power lost in said primary coil and said power applied to said rechargeable power source from said total applied power; and
  - adjusting said total applied power by said external power source as a function of said energy absorbed in said patient.

3. The external power source as in claim 2:
- wherein said power lost in said primary coil is calculated by multiplying a square of said current in said primary coil during said charging by said resistance of said primary coil;
- wherein said external power source supplies power, having a current and a voltage, to said electronic circuitry, wherein said total applied power is calculated by multiplying said current supplied by said external power source during said charging by said voltage supplied by said external power source; and
- wherein said power applied to said rechargeable power source is calculated by multiplying said current applied to said rechargeable power source during said charging by said voltage of said rechargeable power source.

4. The external power source as in claim 3 wherein said voltage supplied by said external power source comprises an RMS voltage, wherein said RMS voltage supplied by said external power source and said current supplied by said external power source have a phase difference and wherein said total applied power is calculated by multiplying said current supplied by said external power source during said charging by said RMS voltage supplied by said external power source and further multiplying by a power factor representative of said phase difference.

5. The external power source as in claim 3 wherein said power lost in said electronic circuitry is determined empirically.

6. The external power source as in claim 5 wherein said power lost in said electronic circuitry is approximately fifteen percent (15%) of said total applied power.

7. A system for controlling energy absorbed in a patient during inductive charging, comprising:
- an implantable medical device, comprising;
  - therapeutic componentry delivering a therapeutic output to said patient;
  - a rechargeable power source operatively coupled to said therapeutic componentry; and
  - a secondary coil operatively coupled to said rechargeable power source; and
- an external power source, comprising:
  - a primary coil;
  - electronic circuitry driving said primary coil; and
  - control circuitry, operatively coupled to said electronic circuitry, configured to control energy absorbed in said patient during inductive charging of said rechargeable power source by:
    - determining a total applied power by said external power source by measuring current applied by said external power source during said charging and an applied voltage of said external power source;
    - determining power lost in said electronic circuitry;
    - determining power lost in said primary coil by determining current in said primary coil during said recharging in view of a resistance of said primary coil;
    - determining power applied to said rechargeable power source by measuring said voltage of said rechargeable power source and current applied to said rechargeable power source during said inductive charging;
    - calculating said energy absorbed in said body by subtracting said power lost in said electronic circuitry, said power lost in said primary coil and said power applied to said rechargeable power source from said total applied power; and
    - adjusting said total applied power by said external power source as a function of said energy absorbed in said patient.

8. The system as in claim 7:
- wherein said power lost in primary coil is calculated by multiplying a square of said current in said primary coil during said charging by said resistance of said primary coil;
- wherein said external power source supplies power, having a current and a voltage, to said electronic circuitry, wherein said total applied power is calculated by multiplying said current supplied by said external power source during said charging by said voltage supplied by said external power source; and
- wherein said power applied to said rechargeable power source is calculated by multiplying said current applied to said rechargeable power source during said charging by said voltage of said rechargeable power source.

9. The system as in claim 8 wherein said voltage supplied by said external power source comprises an RMS voltage, wherein said RMS voltage supplied by said external power source and said current supplied by said external power source have a phase difference and wherein said total applied power is calculated by multiplying said current supplied by said external power source during said charging by said RMS voltage supplied by said external power source and further multiplying by a power factor representative of said phase difference.

10. The system as in claim 7 wherein said power lost in said electronic circuitry is determined empirically.

11. The system as in claim 7 wherein said power lost in said electronic circuitry is approximately fifteen percent (15%) of said total applied power.

12. A device implemented method of determining energy absorbed in a body during inductive charging of an implantable medical device having a rechargeable power source having a voltage and a secondary coil operatively coupled to said rechargeable power source by an external power source having electronic circuitry driving a primary coil, comprising the steps of:
- determining a total applied power by said external power source by measuring current applied by said external power source during said charging and an applied voltage of said external power source;
- determining power lost in said electronic circuitry;
- determining power lost in said primary coil by determining current in said primary coil during said recharging in view of a resistance of said primary coil;
- determining power applied to said rechargeable power source by measuring said voltage of said rechargeable power source and current applied to said rechargeable power source during said inductive charging; and
- calculating, via circuitry, said energy absorbed in said body by subtracting said power lost in said electronic circuitry, said power lost in said primary coil and said power applied to said rechargeable power source from said total applied power.

13. The method as in claim 12:
- wherein said determining power lost in said primary coil step comprises calculating said power lost in primary coil by multiplying a square of said current in said primary coil during said charging by said resistance of said primary coil;
- wherein said external power source supplies power, having a current and a voltage, to said electronic circuitry, wherein said total applied power is calculated by multiplying said current supplied by said external power source during said charging by said voltage supplied by said external power source; and
- wherein said determining said power applied to said rechargeable power source comprises calculating said power applied to said rechargeable power source by multiplying said current applied to said rechargeable power source during said charging by said voltage of said rechargeable power source.

14. The method as in claim 13 wherein said voltage supplied by said external power source comprises an RMS voltage, wherein said RMS voltage supplied by said external power source and said current supplied by said external power source have a phase difference and wherein said determining said total applied power comprises calculating said total applied power by multiplying said current supplied by said external power source during said charging by said RMS voltage supplied by said external power source and further multiplying by a power factor representative of said phase difference.

15. The method as in claim 12 wherein said power lost in said electronic circuitry is determined empirically.

16. The method as in claim 12 wherein said power lost in said electronic circuitry is approximately fifteen percent (15%) of said total applied power.

17. A method for adjusting an amount of energy dissipated in a patient during inductive charging of an implantable medical device having a rechargeable power source having a voltage and a secondary coil operatively coupled to said rechargeable power source by an external power source having electronic circuitry driving a primary coil, comprising the steps of:
- determining a total applied power by said external power source by measuring current applied by said external power source during said charging and an applied voltage of said external power source;
- determining power lost in said electronic circuitry;
- determining power lost in said primary coil by determining current in said primary coil during said recharging in view of a resistance of said primary coil;
- determining power applied to said rechargeable power source by measuring said voltage of said rechargeable power and current applied to said rechargeable power source during said inductive charging;
- calculating said energy absorbed in said patient by subtracting said power lost in said electronic circuitry, said power lost in said primary coil and said power applied to said rechargeable power source from said total applied power; and
- adjusting said total applied power by said external power source as a function of said energy absorbed in said patient.

18. The method as in claim 17:
- wherein said power lost in said primary coil is calculated by multiplying a square of said current in said primary coil during said charging by said resistance of said primary coil;
- wherein said external power source supplies power, having a current and a voltage, to said electronic circuitry, wherein said total applied power is calculated by multiplying said current supplied by said external power source during said charging by said voltage supplied by said external power source; and
- wherein said power applied to said rechargeable power source is calculated by multiplying said current applied to said rechargeable power source during said charging by said voltage of said rechargeable power source.

19. The method as in claim 18 wherein said voltage supplied by said external power source comprises an RMS voltage, wherein said RMS voltage supplied by said external power source and said current supplied by said external power source have a phase difference and wherein said determining said total applied power comprises calculating said total applied power by multiplying said current supplied by said external power source during said charging by said RMS voltage supplied by said external power source and further multiplying by a power factor representative of said phase difference.

20. The method as in claim 17 wherein said power lost in said electronic circuitry is determined empirically.

21. The method as in claim 17 wherein said power lost in said electronic circuitry is approximately fifteen percent (15%) of said total applied power.

* * * * *